United States Patent

Best et al.

[11] Patent Number: 6,137,294
[45] Date of Patent: Oct. 24, 2000

[54] PREDICTION OF BULK DENSITY OF PARTICULATES WITH A CORRELATION BASED ON MOISTURE CONTENT

[75] Inventors: Michael Howard Best, Monroeville; David Michael Rohaus, Harrison City, both of Pa.

[73] Assignee: USX Corporation, Pittsburgh, Pa.

[21] Appl. No.: 09/234,920

[22] Filed: Jan. 21, 1999

[51] Int. Cl.$^7$ ................................................. G01R 27/04
[52] U.S. Cl. .................................................... 324/640
[58] Field of Search .................................. 324/640, 639; 208/401, 402

[56] References Cited

U.S. PATENT DOCUMENTS

| | | | |
|---|---|---|---|
| 3,678,268 | 7/1972 | Reim et al. | 250/43.5 D |
| 4,304,636 | 12/1981 | Kestner et al. | 201/20 |
| 4,450,046 | 5/1984 | Rice et al. | 201/41 |
| 4,475,080 | 10/1984 | Walker | 324/640 |
| 4,506,541 | 3/1985 | Cunningham | 73/32 R |
| 4,766,319 | 8/1988 | Regimand | 250/390 |
| 5,333,493 | 8/1994 | Cutmore | 73/73 |
| 5,435,813 | 7/1995 | Evans | 44/620 |
| 5,767,685 | 6/1998 | Walker | 324/640 |

OTHER PUBLICATIONS

Robert H. Lux and Alan D. Strauss, Automated Bulk Density Control System for Blended Coal at the Burns Harbor Coke Plant (1996).
The Making, Shaping and Treating of Steel (Tenth Edition) United States Steel (pp. 146–148) (1985).

*Primary Examiner*—Safet Metjahic
*Assistant Examiner*—James Kerveros

[57] ABSTRACT

A method for predicting the bulk density of coal after it is dropped from a known height into a container from measurements of bulk density and moisture content of the coal before it is dropped into the container. The method includes obtaining a plurality of samples of coal, measuring the bulk density of each coal sample by directing nuclear radiation through the coal, subsequently dropping each sample from said known height in a test facility and measuring the bulk density of each coal sample after drop, measuring the moisture content of each coal sample, determining a correlation between the bulk density of said coal samples after drop with the bulk density determined before drop and the moisture content, and predicting the bulk density of coal after drop into a container from subsequent measurement of the bulk density and moisture content and the previously determined correlation from test facility measurements.

6 Claims, 4 Drawing Sheets

PREDICTION OF BULK DENSITY OF PARTICULATES WITH A CORRELATION BASED ON MOISTURE CONTENT

TECHNICAL FIELD

This invention relates to prediction of the bulk density of a plurality of particulates after the particulates are dropped from a known height, and particularly to predicting the bulk density of said particulates from a correlation based on bulk density and moisture content of the particulates measured prior to drop, particularly while the particulates are on a traveling conveyor belt.

BACKGROUND ART

It is important to control the bulk density of coal charged into ovens for the production of metallurgical coke used in the iron blast furnace. Bulk density affects proper heating of the coal to produce coke, the level of coal in the oven, the pressure on the walls of by-product coke ovens during the coking process, and the strength of the coke produced. To control the bulk density of a coal blend being prepared for charging into a coke oven, common practice is to measure the bulk density of a coal sample taken from coal on a conveyor belt as it travels from a hammermill, or some other machine designed to pulverize the coal, to coal bunkers for storage prior to charging. The bulk density of the coal is adjusted based on a measured value by adding diesel grade oil, similar oils or other substances in varying amounts to the coal to obtain a desired bulk density value when the coal is subsequently dropped from a known height by a larry car as it is charged into the coke oven. In a manual system, bulk density measurements are made regularly by taking a sample of the coal from the conveyor belt and pouring the sample from a known height into a box of known volume, and then weighing the coal to arrive at a bulk density value in pounds per cubic foot. The flow rate of oil being added to the coal is adjusted manually as required to obtain a predicted post-drop bulk density that is equal to the desired value when the coal is charged into the coke oven.

There are two systems available for automatic control of the bulk density of coal in preparation for the production of metallurgical coke, namely weigh belts and nuclear gamma ray units. The weigh-belt system is relatively expensive to operate and will not be discussed further. With the gamma-ray system, the bulk density of the coal on the conveyor belt is measured as the coal leaves a pulverizer or coal mixer. In both systems the amount of oil or other substance needed to adjust the bulk density is automatically regulated to attain the desired density value. The nuclear gamma-ray measurement system, while complex is capable of performing with an accuracy of plus or minus one pound per cubic foot (i.e. plus or minus 16 kilograms per cubic meter). However, the gamma-ray system is reportedly influenced by a number of factors as described in *The Making, Shaping & Treating of Steel,* 10th Edition, pages 146–148. Some of the most important factors reported in the reference are: (1) the depth of the coal on the belt as it passes under the radioactive source; (2) changes in the radiation-absorption coefficient of the coal; (3) dust or other material in the signal path; (4) temperature of the detector; (5) thickness and tension of the belt; and (6) size consistency, moisture content and temperature of the coal. While moisture content has been generally recognized as a factor in the measurement of bulk density using gamma radiation, it generally is believed that the effect is small based on the difference in the absorption coefficient of gamma radiation by water and coal.

U.S. Pat. No. 3,678,268 to Reim et al, discloses a gamma radiation bulk density gauge for measuring the bulk density of coal on a conveyor belt and a system for controlling the bulk density by varying water and oil addition rates based on the bulk density measurements. The rate of water addition is controlled to bring the rate of oil addition within a desired range. Prior to leveling the coal on a second conveyor and measuring the bulk density, the coal is dropped from a first conveyor onto the second conveyor. The height of the first conveyor is adjusted to make the drop substantially the same as the drop the coal undergoes in the coke oven. Where the conveyor system cannot be adjusted to simulate the drop into the oven, alternate devices are described for simulating the drop, e.g. the sled and weights shown in FIGS. 6–8 and the paddle wheel assembly of FIG. 9 of the reference. This reference does not disclose prediction of the post-drop coal bulk density by the measurement of the coal bulk density and moisture content prior to drop, for example while the coal is on a conveyor belt, nor the correlation of such measured bulk density and moisture content with the predicted post-drop bulk density. R. H. Lux and A. D. Strauss, 1996 Ironmaking Conference Proceedings, pages 515–520 also describe another automated bulk density control system in which gamma radiation bulk density gauges are used.

A gauge for continuously measuring the moisture content of coal of varying thickness on a conveyor belt using microwaves is disclosed in U.S. Pat. No. 5,333,493 to Cutmore. A gauge that measures both moisture content and bulk density of coal is described in U.S. Pat. No. 4,766,319. This gauge uses a low activity neutron radiation source to measure moisture and a low activity gamma radiation source to measure bulk density. A correction signal is applied to the density measurement based on the moisture content to account for gamma radiation produced by a thermal neutron capture reaction which occurs when neutron radiation is used to measure moisture content of the coal. The reference does not suggest prediction of post-drop bulk density based on a correlation of bulk density and moisture content measurements made while the particulates are at rest before drop, particularly while the particulates are at rest on a conveyor belt.

Other miscellaneous references are: U.S. Pat. Nos. 4,304,636; 4,450,046; 4,506,541 and 5,435,541.

DISCLOSURE OF INVENTION

According to this invention, a method is provided for predicting the bulk density of particulate material, after the particulate material is dropped from a known height, as a function of the measured bulk density and moisture of the particulate material prior to drop. Preferably the bulk density before drop is measured by nuclear radiation, most preferably gamma radiation, directed from a source through the particulates. The amount of radiation passing through the particulates is detected at a location opposite the source as a measure of the bulk density. Preferably the moisture content is measured by directing microwaves through the particulates and determining the amount of microwaves passing therethrough. In a preferred form the bulk density and moisture contents are measured continuously or periodically at spaced time intervals. Most preferably the bulk density and moisture measurements are made on particulate material being conveyed on a traveling conveyor belt. The method also includes controlling the bulk density of the particulates by adding at least one substance, preferably a liquid substance, to the particulates to adjust the predicted post-drop bulk density to a desired value based on the bulk density measurement and moisture measurement of the particulates prior to drop, particularly while the particulates are on a traveling conveyor belt.

MODES FOR CARRYING OUT THE INVENTION

Figure 1:
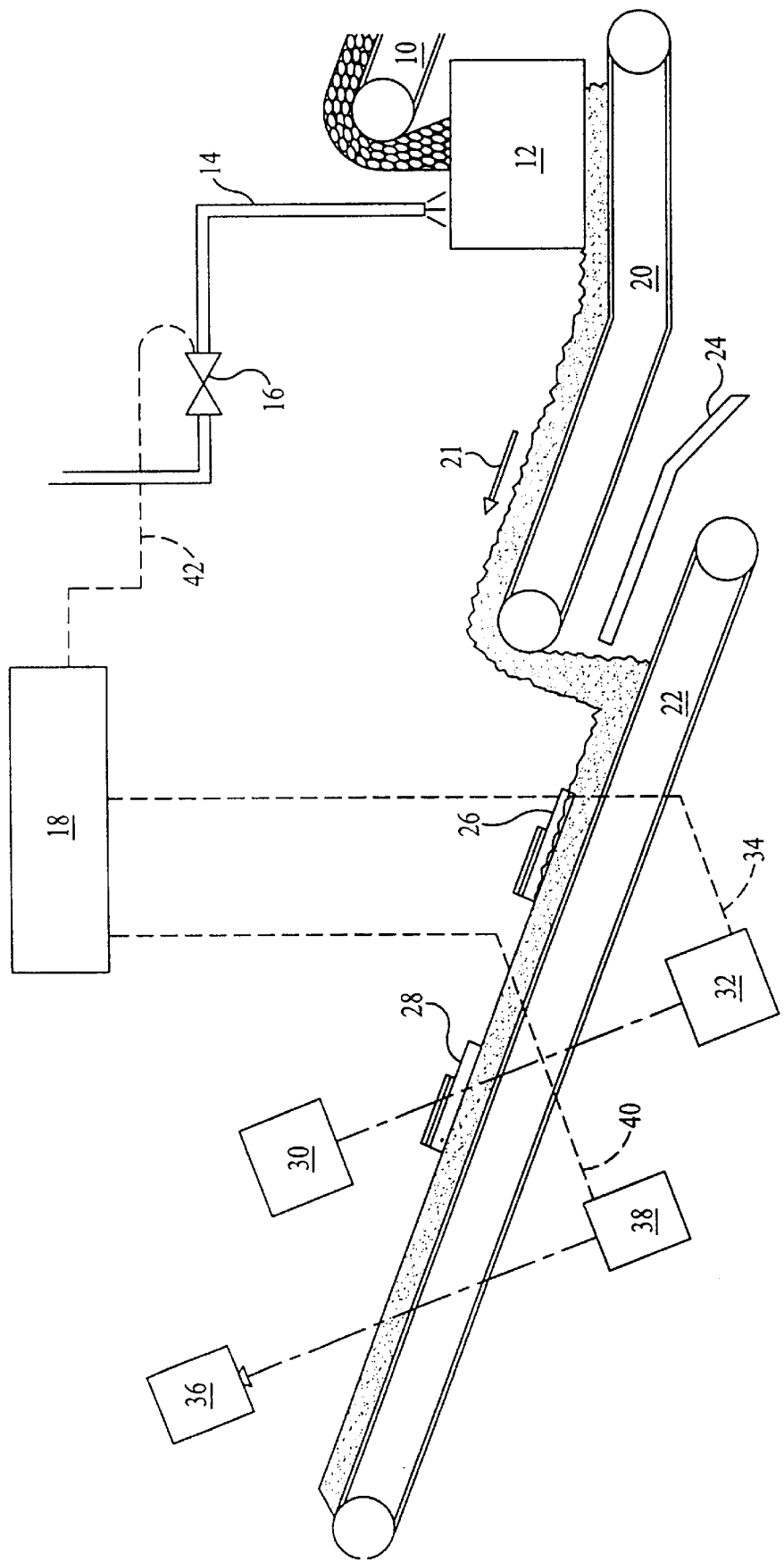
FIG. 1 is a schematic diagram of the apparatus for controlling the bulk density of coal being prepared for charging into a coke oven.

Referring to FIG. 1, large coal particles are transported on conveyor belt 10 to a pulverizer or hammermill 12 where the coal is crushed to smaller size suitable for charging into an oven (not shown) for producing metallurgical coke. A feed system is provided to add oil or another substance to the coal as it is crushed in the hammermill so that the oil or other substance becomes well mixed with the coal. The feed system includes pipe 14, flow control valve 16 and programmable controller 18 and a source of oil or other substance (not shown). The amount of oil or other substance added is dependent upon the deviation of a predicted post-drop coal density and a desired value. The feed system may be placed at other locations, for example, subsequent to the hammermill, to add the oil while the coal is on one of the conveyor belts. Crushed coal mixed with oil is transported from the hammermill by conveyor 20 in a direction shown by arrow 21 and dropped onto conveyor 22. An automatic sampling device is schematically illustrated at 24 for obtaining samples of the coal as it is dropped from conveyor 20 to conveyor 22. The height of the drop of coal from conveyor 20 to conveyor 22 in our system is not adjustable and does not correspond to the distance of the drop of the coal into the coke ovens. For purposes of the claims the phrase "measurement prior to drop" includes measurements made on the particulates under various conditions, for example, when the particulates are in a container, or on a traveling conveyor belt, and regardless of prior handling of the particulates, such as a drop from one conveyor to another. A first coal-leveling device of conventional known design is illustrated at 26 for leveling the coal on the belt to an approximate desired height. A second coal-leveling device of conventional known design is illustrated at 28 for leveling the coal on the belt to the final desired height. The leveling devices assure that the coal on the conveyor belt is of a known, uniform depth prior to its passing before the bulk density and moisture measurement gauges. A nuclear gamma radiation gauge is provided for measuring the bulk density of the coal on the belt and includes a gamma radiation source 30 and a gamma radiation detector 32. An electrical signal is transmitted by line 34 from detector 32 to programmable controller 18 indicating the amount of gamma radiation that has passed through the coal as a measure of the bulk density of the coal on the belt. A microwave moisture gauge is provided to measure the moisture of the coal on the belt and includes a microwave source 36 and a microwave detector 38. An example of a suitable microwave moisture measurement device is described in U.S. Pat. No. 5,333,493 to Cutmore, the specification of which is incorporated herein and made a part hereof. An electrical signal is transmitted by line 40 from detector 38 to programmable controller 18 indicating the phase shift and attenuation changes of the microwaves that have passed through the coal and therefore the amount of moisture in the coal. Programmable controller 18 calculates the predicted post-drop bulk density based on the bulk density and moisture content of the coal on conveyor 22 and determines the oil flow adjustment required to bring the predicted bulk density to the desired value. A signal based on these calculations is transmitted from programmable controller 18 on line 42 to valve 16 to adjust the oil flow to the proper rate to obtain the desired post-drop bulk density.

Figure 4:
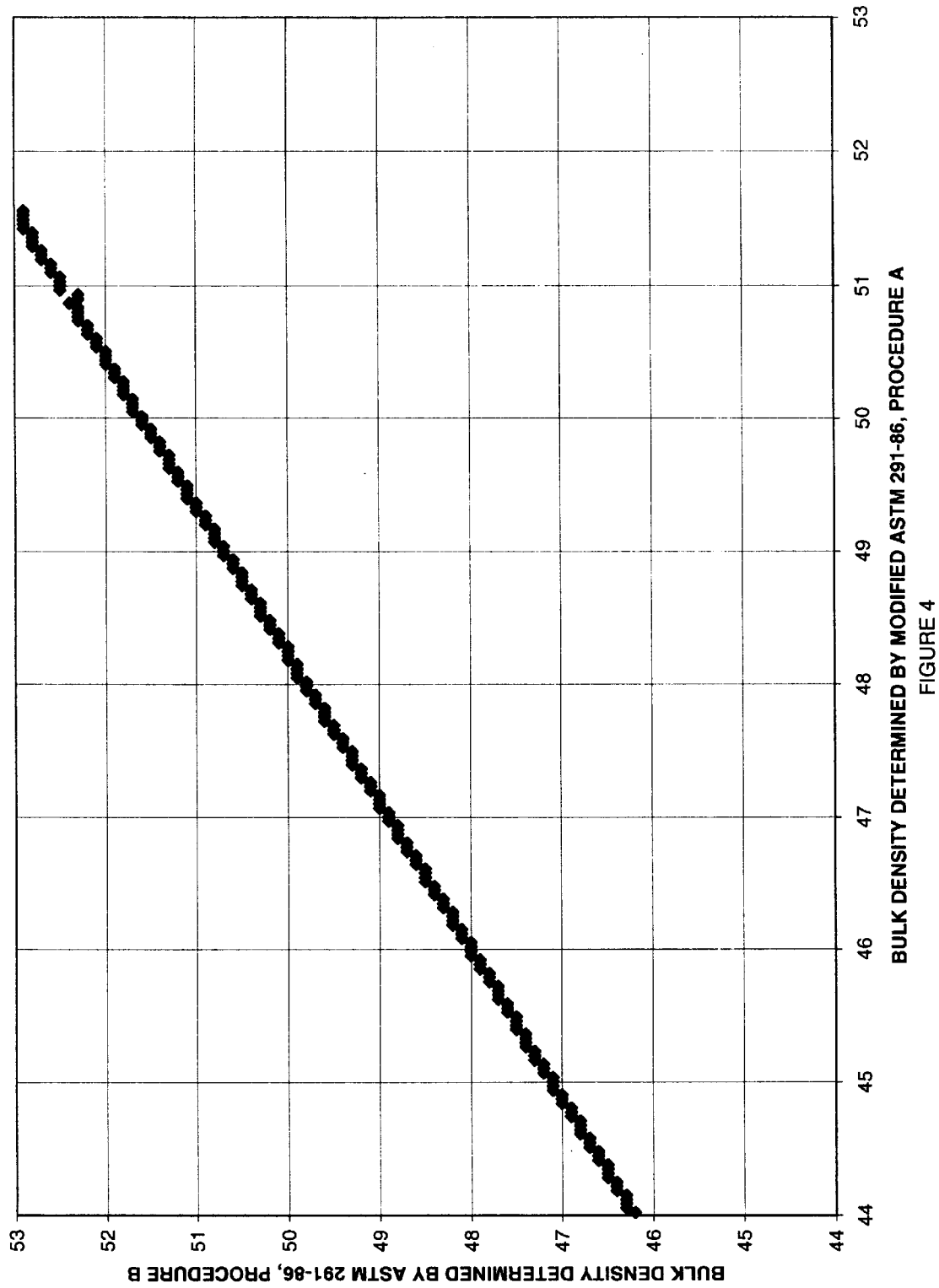
FIG. 4 is a graph of a previously determined correlation of the bulk density as determined by modified ASTM 291-86, Procedure A, with the bulk density determined by ASTM 291-86, Procedure B.

A series of tests were run in which samples of coal were obtained using the automatic sampling device 24. Nuclear gamma radiation instrument readings were obtained at the same time as the sample was being taken. The actual weighed post-drop bulk density was determined on each sample using a modified test based on Procedure A of ASTM Method 291-86. The ASTM method is modified in that the size of the container is ⅔ of a cubic foot versus a one cubic foot container in the ASTM test. The apparent coal bulk density determined using the modified ASTM test is converted to a post-drop coal bulk density corresponding to the bulk density determined by Procedure B of ASTM Method 291-86 based on a relationship developed from a plurality of tests carried out before the present invention. The relationship between the apparent coal bulk density determined by the modified ASTM test and the Procedure B test is shown in FIG. 4. The actual coal moisture was measured by placing a split of the coal sample from the drop test into an oven for at least four hours. The sample weight loss after drying was determined to indicate actual moisture content. From over 250 such samples and tests a correlation was found between the post-drop bulk density, i.e. the bulk density found from the modified ASTM tests as converted to the bulk density of ASTM test Procedure B, and bulk density and moisture measurements made while the coal was on the conveyor. The basic correlation found on our tests was as follows:

$$BD_{AD} = A + BD_{BD} \times B + \% \ M \times C$$

Where $BD_{AD}$=Post-drop Bulk Density $BD_{BD}$=Bulk Density Mesurement before drop (i.e. on the conveyor belt)

M=Moisture in wt. %

A=a first constant

B=a second constant

C=a third constant

Actual values of the constants will depend on the particular conditions under which the tests are performed. We determined the following values for the constants under our test conditions:

A=21.23

B=0.58

C=−0.18

Figure 2:
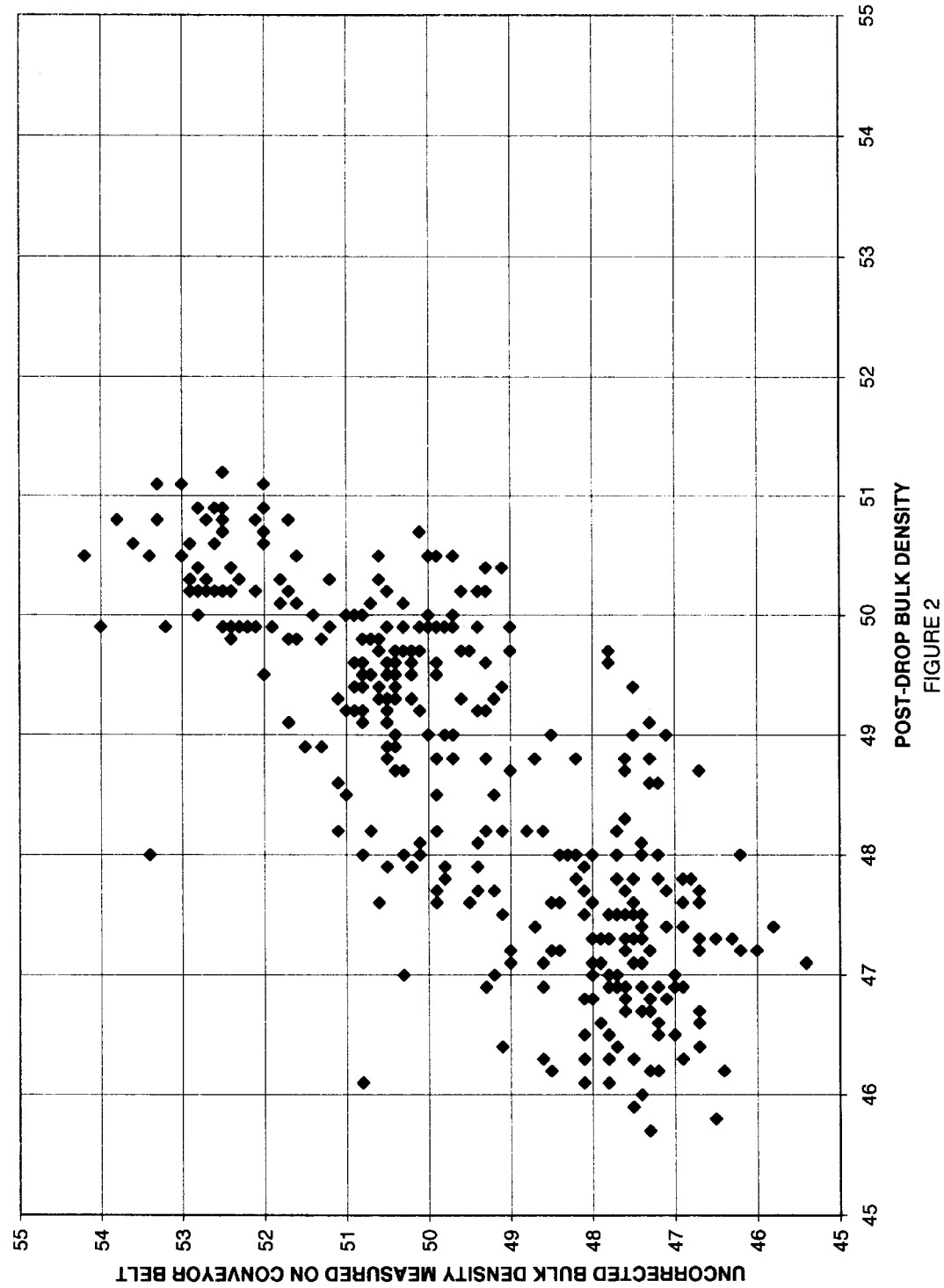
FIG. 2 is a graph of actual weighed post-drop bulk density versus uncorrected bulk density measured by a nuclear gamma radiation gauge while the coal is on a traveling conveyor belt.
Figure 3:
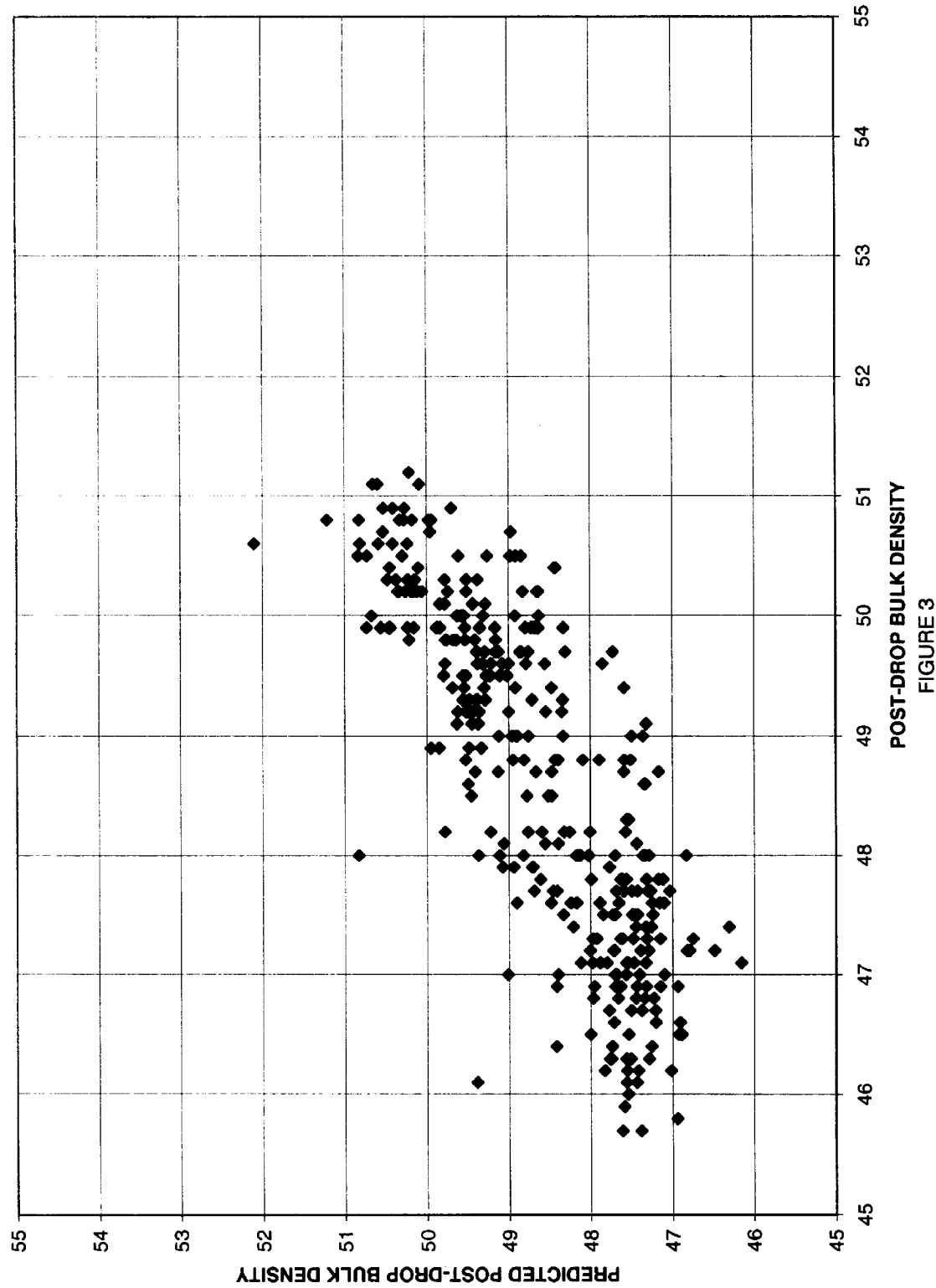
FIG. 3 is a graph of actual weighed post-drop bulk density versus a predicted post-drop bulk density based on a previously determined correlation equation that relates predicted post-drop bulk density to coal bulk density and moisture content measured while the coal is on a traveling conveyor belt, the coal bulk density on the conveyor being determined using a nuclear gamma radiation gauge.

The effect of the correlation on the variability of the predicted post-drop bulk density is illustrated by comparing the graphs in FIG. 2 and FIG. 3. FIG. 2 shows actual post-drop bulk density versus the coal bulk density measured on the belt. FIG. 3 shows a substantial reduction of variability in a graph of actual post-drop bulk density versus predicted post-drop bulk density based on measured bulk density and moisture content while the coal is on a conveyor belt.

We have also found that a separate correlation equation may provide the best prediction of post-drop bulk density for the coal being conveyed to different coal bunkers. For example, for the coal being conveyed to the No. 5 Bunker at the Clairton, Pa. Plant of the assignee, a non-linear correlation equation was found to provide the best fit, as follows:

$$BD_{AD}=30.79+0.38(BD_{BD})-0.0086\% M-0.07184(\% M-\% M_{AV})^2$$

Where $\% M_{AV}$=Average Percent Moisture on all tests.

The data for coal being conveyed to the No. 7 Bunker at the Clairton Plant indicated that a linear equation provided the best fit, as follows:

$$BD=33.93+0.31(BD_{BD})-0.1806(\% M)$$

It should also be noted that the addition of waste substances, such as tar, to the coal has been found to affect the measurements to some extent. The affect of tar did not appear to be consistent but did influence the correlation on some occasions.

Thus, the specific equation and the form of the correlation equation may vary depending on the bulk density measurement instrument used, the type and thickness of the conveyor belt, the height of coal on the belt after passing through the leveling devices, the angle of the nuclear source and detector with respect to the coal, the strength of the nuclear source and other conditions. The actual form of correlation applicable to any given test situation may be determined by known mathematical correlation techniques.

Industrial Applicability

As a result of the invention it is possible to decrease the variability of the bulk density of coal being charged into a coke oven and to increase the aim bulk density without problems attendant with prior control methods. Thus, the productivity of the coke ovens may be increased, more uniform heating and more stable operation of the coke ovens can be obtained, and the quality of the coke produced is enhanced.

What is claimed is:

1. A method for predicting the post-drop bulk density of coal in particulate form that is to be dropped from a known height into a container from one or more bulk density measurements of said coal prior to drop into the container, said method comprising:
   (a) conducting a series of tests which include:
       (i) obtaining a plurality of samples of coal and measuring the bulk density of each coal sample by directing nuclear radiation from a source through the coal sample and detecting the amount of radiation passing through the coal sample opposite the source;
       (ii) dropping each coal sample from a height about equal to the known height of drop into said container and measuring the bulk density of the coal sample after drop by weighing the sample;
       (iii) measuring the moisture content of each coal sample;
       (iv) determining a correlation between the bulk density of the coal samples after drop as a function of bulk density measurements made by nuclear radiation before drop and moisture content; and
   (b) subsequently from coal that is on a traveling conveyor taking at least one measurement of the moisture content of the coal using a microwave device and at least one bulk density measurement of the coal using a nuclear radiation device; and
   (c) predicting the bulk density of the coal after it is dropped from said known height into the container from the bulk density and moisture content measured on the conveyor and the previously determined correlation from said series of tests on said samples.

2. The method of claim 1 wherein the basic correlation equation is as follows:

$$BD_{AD}=A+BD_{BD}\times B+\% M\times C$$

where
   $BD_{AD}$=post-drop bulk density
   $BD_{BD}$=bulk density measurement on the conveyor
   M=moisture content measurement on the conveyor
   A=a first constant
   B=a second constant
   C=a third constant.

3. The method of claim 2 wherein the basic correlation equation includes a non-linear term as follows:

$$BD_{AD}=A+BD_{BD}\times B+\% M\times C+(\% M-M_{AV})^2\times D$$

where
   $M_{AV}$=Average Percent Moisture content measurement on the conveyor,
   D=a fourth constant.

4. The method of either claim 2 or 3 in which a substance is added to the coal based on the predicted post-drop bulk density to adjust the post-drop bulk density to a desired value.

5. The method of claim 4 wherein measurements of bulk density and moisture content of the coal on the conveyor is made periodically and substantially simultaneously.

6. The method of claim 4 wherein measurements of bulk density and moisture content of the coal on the conveyor are made continuously.

* * * * *